United States Patent
Utagawa et al.

(10) Patent No.: US 10,433,721 B2
(45) Date of Patent: Oct. 8, 2019

(54) OPHTHALMIC APPARATUS AND CONTROL METHOD FOR THE SAME

(71) Applicant: CANON KABUSHIKI KAISHA, Tokyo (JP)

(72) Inventors: Tsutomu Utagawa, Yokohama (JP); Hiroshi Imamura, Kyoto (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/063,998

(22) Filed: Mar. 8, 2016

(65) Prior Publication Data

US 2016/0262607 A1 Sep. 15, 2016

(30) Foreign Application Priority Data

Mar. 13, 2015 (JP) .................. 2015-051045

(51) Int. Cl.
*A61B 3/00* (2006.01)
*A61B 3/10* (2006.01)
*A61B 3/14* (2006.01)
*G02B 21/00* (2006.01)

(52) U.S. Cl.
CPC .......... *A61B 3/0025* (2013.01); *A61B 3/1025* (2013.01); *A61B 3/14* (2013.01); *G02B 21/0028* (2013.01)

(58) Field of Classification Search
CPC ....... A61B 3/0025; A61B 3/1025; A61B 3/14; A61B 3/0041; A61B 3/0058
See application file for complete search history.

(56) References Cited

U.S. PATENT DOCUMENTS

| 2012/0070059 A1 | 3/2012 | Furukawa et al. |
| 2012/0218515 A1 | 8/2012 | Imamura |
| 2013/0058553 A1 | 3/2013 | Yonezawa et al. |

(Continued)

FOREIGN PATENT DOCUMENTS

| CN | 101254091 A | 9/2008 |
| CN | 101254091 B | 8/2010 |
| JP | 2012176093 A | 9/2012 |

(Continued)

OTHER PUBLICATIONS

Extended European Search Report issued in connection with EP Application No. 16159315.7 dated Sep. 13, 2016, 9 pages.

(Continued)

*Primary Examiner* — Darryl J Collins
*Assistant Examiner* — Journey F Sumlar
(74) *Attorney, Agent, or Firm* — Carter, DeLuca & Farrell LLP

(57) ABSTRACT

Provided is an ophthalmic apparatus, including: an acquisition unit configured to acquire a confocal image and a nonconfocal image of an eye to be inspected (E); a first detection unit configured to detect a photoreceptor cell of the eye to be inspected (E) from the confocal image; a second detection unit configured to detect a photoreceptor cell of the eye to be inspected (E) from the nonconfocal image; and a display unit configured to compare the photoreceptor cell detected by the first detection unit and the photoreceptor cell detected by the second detection unit with each other to display a result of the comparison on a screen.

7 Claims, 9 Drawing Sheets

(56) References Cited

U.S. PATENT DOCUMENTS

2015/0002812 A1 1/2015 Yoshihara et al.
2016/0235294 A1* 8/2016 Utagawa .............. A61B 3/1025

FOREIGN PATENT DOCUMENTS

JP 2013169295 A 9/2013
WO 2016009603 A1 1/2016

OTHER PUBLICATIONS

Sulai et al.,"Visualization of retinal vascular structure and perfusion with a nonconfocal adaptive optics scanning light ophthalmoscope", J. Opt. Soc. Am. A, vol. 31, No. 3, pp. 569-579, 2014.

Scoles et al., "In vivo Imaging of Human Cone Photoreceptor Inner Segments", IOVS, vol. 55, No. 7, pp. 4244-4251, 2014.

Chinese First Office Action for Chinese Appln. No. 201610141676.1 dated Oct. 11, 2017.

Scoles et al., In Vivo Imaging of Human Cone Photoreceptor Inner Segments, Investigative Ophthalmology & Visual Science, vol. 55, No. 7, pp. 4244-4251 (Jul. 2014).

Scoles et al., "In vivo dark-field imaging of the retinal pigment epithelium cell mosaic", Biomedical Optics Express, vol. 4, No. 9, pp. 1710-1723.

Japanese Office Action cited in JP Application No. 2015051045 dated Dec. 11, 2018, with English translation, 6 pages.

Notice of Reasons for Refusal issued by the Japanese Patent Office dated Jul. 2, 2019 in corresponding Japanese Patent Application No. 2015-051045, with English translation.

* cited by examiner

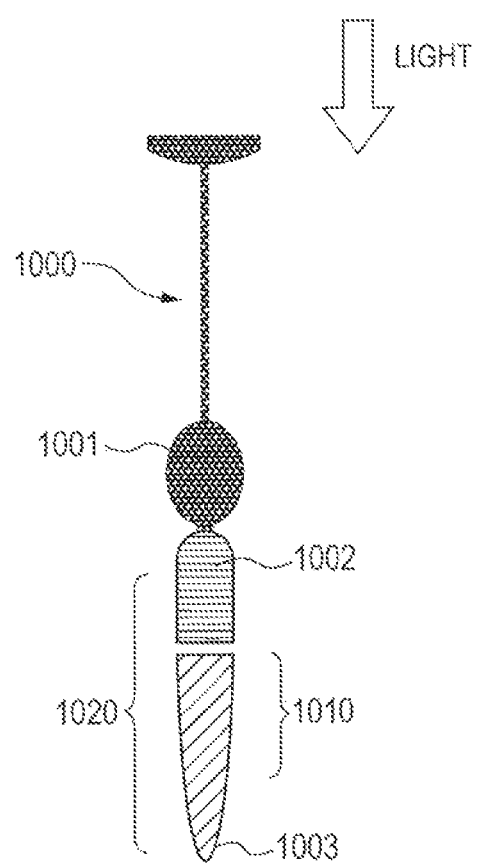

OPHTHALMIC APPARATUS AND CONTROL METHOD FOR THE SAME

BACKGROUND OF THE INVENTION

1. Field of the Invention

The present invention relates to an ophthalmic apparatus configured to photograph an image of an eye to be inspected and a control method for the ophthalmic apparatus.

2. Description of the Related Art

The inspection of an eye portion has been widely conducted for the purpose of diagnosing and treating lifestyle-related diseases and diseases that are leading causes of blindness in early stages. A scanning laser ophthalmoscope (SLO), which is an ophthalmic apparatus using a principle of a confocal laser microscope, is an apparatus configured to perform raster scanning on a fundus of the eye with laser light that is measuring light, and acquire a planar image of the fundus of the eye based on the intensity of return light of the measuring light with high resolution at high speed. For example, through the detection of only light having passed through a pinhole, this apparatus can image only return light at a particular depth position to acquire an image with a higher contrast compared to that of a general fundus camera and the like. Such an apparatus configured to photograph a planar image is hereinafter referred to as "SLO apparatus", and the planar image is hereinafter referred to as "SLO image".

In recent years, in the SLO apparatus, it has become possible to acquire an SLO image of a retina with improved lateral resolution by increasing a beam diameter of measuring light. However, along with the increase in the beam diameter of the measuring light, there occurs a problem of decreases in an S/N ratio and the resolution of an SLO image of a retina due to an aberration of an eye to be inspected when the SLO image is acquired.

In order to solve the problem, there is developed an adaptive optics SLO apparatus including an adaptive optics (AO) system, in which an aberration of an eye to be inspected is measured by a wavefront sensor in real time, and aberrations of measuring light and return light thereof generated in the eye to be inspected are corrected by a wavefront correction device. The adaptive optics SLO apparatus including an adaptive optics system is hereinafter referred to as "AO-SLO apparatus".

With such an AO-SLO apparatus, it is possible to acquire an SLO image having high lateral resolution. Further, the AO-SLO apparatus can acquire the AO-SLO image having high lateral resolution as a moving image, and, for example, in order to observe hemodynamics non-invasively, can measure the moving speed of blood corpuscles in a capillary vessel and the like through extraction of a retinal vessel from each frame. Further, when observing photoreceptor cells, the AO-SLO apparatus sets a focus position to the vicinity of an outer surface of the retina, to thereby photograph an SLO image.

However, in the SLO image, in a confocal image obtained by photographing an inner layer of the retina, a noise signal is strong owing to the influence of light reflecting from a nerve fiber layer, and hence it is difficult to observe a blood vessel wall and detect a wall boundary in some cases. In view of the foregoing, in recent years, for example, a method involving obtaining scattering light by changing the diameter, shape, and position of a pinhole arranged in front of a photo-receiving unit and observing a nonconfocal image thus obtained has come to be used (see, for example, Sulai, Dubra et al.; "Visualization of retinal vascular structure and perfusion with a nonconfocal adaptive optics scanning light ophthalmoscope", J. Opt. Soc. Am. A, Vol. 31, No. 3, pp. 569-579, 2014). In the SLO image, in the nonconfocal image, a focus depth is large, and hence an object having irregularities in a depth direction, such as a blood vessel, can be observed easily. Further, light reflected from the nerve fiber layer is not easily received directly, and hence noise can be reduced.

Further, the following has been found. Even in the case where photoreceptor cells in the outer layer of the retina are observed, hitherto, a photoreceptor outer segment is mainly imaged in the confocal image, whereas irregularities of a photoreceptor inner segment are imaged in the nonconfocal image (see, for example, Scoles, Dubra et al.; "In vivo Imaging of Human Cone Photoreceptor Inner Segment", IOVS, Vol. 55, No. 7, pp. 4244-4251, 2014). That is, hitherto, in "Sulai, Dubra et al.; "Visualization of retinal vascular structure and perfusion with a nonconfocal adaptive optics scanning light ophthalmoscope", J. Opt. Soc. Am. A, Vol. 31, No. 3, pp. 569-579, 2014", there is a disclosure of a technology of acquiring a nonconfocal image of a retinal vessel through use of an AO-SLO apparatus. In addition, in "Scoles, Dubra et al.; "In vivo Imaging of Human Cone Photoreceptor Inner Segment", IOVS, Vol. 55, No. 7, pp. 4244-4251, 2014, there is a disclosure of a technology of concurrently acquiring a confocal image and a nonconfocal image through use of an AO-SLO apparatus.

In the case of photographing a fine image of a fundus of an eye, the signal intensity of an image to be acquired is significantly larger in a photographing apparatus using a confocal optical system than in a photographing apparatus using a nonconfocal optical system. Therefore, in the case of photographing a fundus image, photographing is generally performed by the photographing apparatus using a confocal optical system.

However, in the photographing apparatus using a confocal optical system, a focus depth is small. Therefore, there is a problem in that, in the case of analyzing a photographed fundus image, only image information on a narrow region in a depth direction of a photoreceptor cell is obtained, and it is difficult to grasp a detailed state of the photoreceptor cell of an eye to be inspected.

The present invention has been made in view of the above-mentioned problem, and it is an object of the present invention to provide a mechanism capable of grasping a detailed state of a photoreceptor cell of an eye to be inspected.

SUMMARY OF THE INVENTION

According to one embodiment of the present invention, there is provided an ophthalmic apparatus, including: an acquisition unit configured to acquire a confocal image and a nonconfocal image of an eye to be inspected; a first detection unit configured to detect a photoreceptor cell of the eye to be inspected through use of the confocal image; a second detection unit configured to detect a photoreceptor cell of the eye to be inspected through use of the nonconfocal image; a first comparison unit configured to compare the photoreceptor cell detected by the first detection unit and the photoreceptor cell detected by the second detection unit with each other; and a display unit configured to display a comparison result obtained by the first comparison unit on a screen.

According to another embodiment of the present invention, the ophthalmic apparatus further includes a second comparison unit configured to compare a first comparison result and a second comparison result with each other, the first comparison result being a comparison result between the photoreceptor cell detected by the first detection unit and the photoreceptor cell detected by the second detection unit, which is obtained by the first comparison unit at a first time, the second comparison result being a comparison result between the photoreceptor cell detected by the first detection unit and the photoreceptor cell detected by the second detection unit, which is obtained by the first comparison unit at a second time different from the first time, the display unit being configured to further display a comparison result obtained by the second comparison unit on the screen.

Further, according to another embodiment of the present invention, there is provided an ophthalmic apparatus, including: an acquisition unit configured to acquire a confocal image and a nonconfocal image of an eye to be inspected; a first detection unit configured to detect a photoreceptor outer segment of the eye to be inspected through use of the confocal image; a second detection unit configured to detect a photoreceptor inner segment and a photoreceptor outer segment of the eye to be inspected through use of the nonconfocal image; and a display unit configured to display a state of each photoreceptor cell of the eye to be inspected based on a detection result obtained by the first detection unit and a detection result obtained by the second detection unit. Further, according to another embodiment of the present invention, there is provided an ophthalmic apparatus, including: an acquisition unit configured to acquire a confocal image and a nonconfocal image of an eye to be inspected; a first detection unit configured to detect a photoreceptor cell of the eye to be inspected through use of the confocal image; a second detection unit configured to detect a photoreceptor cell of the eye to be inspected through use of the nonconfocal image; and a display unit configured to display a detection result of the photoreceptor cell obtained by the first detection unit and a detection result of the photoreceptor cell obtained by the second detection unit on the same screen.

Further, the present invention encompasses a control method for the above-mentioned ophthalmic apparatus, and a program for causing a computer to perform the control method.

Further features of the present invention will become apparent from the following description of exemplary embodiments with reference to the attached drawings.

BRIEF DESCRIPTION OF THE DRAWINGS

FIG. 10 is a diagram for illustrating a schematic structure of a photoreceptor cell of an eye to be inspected according to the first embodiment of the present invention.

DESCRIPTION OF THE EMBODIMENTS

Modes (embodiments) for carrying out the present invention are now described with reference to the drawings.

First Embodiment

First, a first embodiment of the present invention is described.

In this embodiment, an apparatus including the above-mentioned AO-SLO apparatus is described as an ophthalmic apparatus according to the present invention. The AO-SLO apparatus includes an adaptive optics system, and is an apparatus configured to photograph an SLO image (AO-SLO image) having high lateral resolution of a fundus of an eye to be inspected. In addition, for the purpose of aiding acquisition of the AO-SLO image, the ophthalmic apparatus according to this embodiment includes a wide field scanning laser ophthalmoscope (WF-SLO) apparatus configured to photograph an SLO image having a wide field angle (WF-SLO image) larger than that of an AO-SLO image, a beacon device configured to measure an aberration occurred in an eye to be inspected, a fixation target display device configured to guide a line of sight of an eye to be inspected so as to adjust a photographing position, and an anterior ocular segment observation device configured to grasp an incident position of measuring light.

Specifically, in the ophthalmic apparatus according to this embodiment, the AO-SLO apparatus is configured to acquire an SLO image by correcting an optical aberration of an eye to be inspected through use of a spatial light modulator. With the AO-SLO apparatus, a good SLO image can be acquired regardless of a diopter scale and the optical aberration of the eye to be inspected. Note that, in this embodiment, in order to photograph an SLO image having high lateral resolution, the AO-SLO apparatus including the adaptive optics system is used. However, an SLO apparatus not including the adaptive optics system may be used as long as the configuration of the optical system can realize high resolution.

<Entire Configuration of Ophthalmic Apparatus>

Figure 1A:
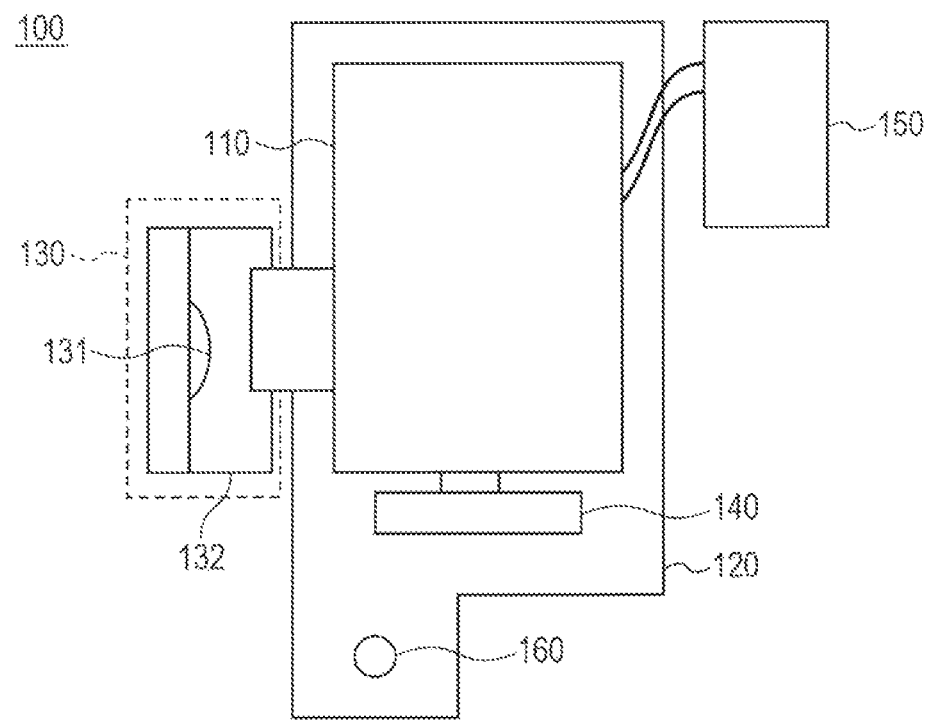
FIG. 1A and FIG. 1B are each a diagram for illustrating an example of an entire configuration of an ophthalmic apparatus according to a first embodiment of the present invention.
Figure 1B:
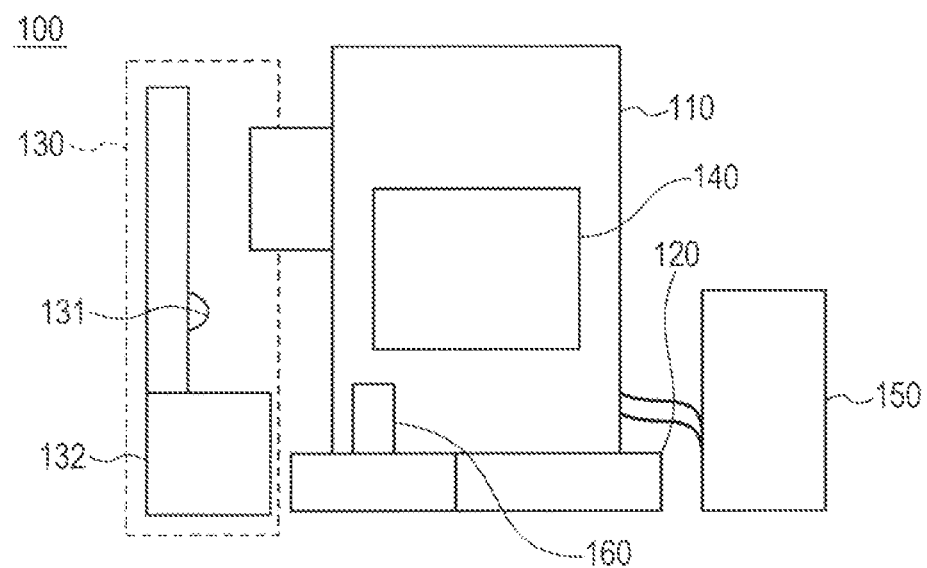

FIG. 1A and FIG. 1B are each a diagram for illustrating an example of an entire configuration of an ophthalmic apparatus 100 according to the first embodiment of the present invention. Specifically, FIG. 1A is a diagram of the ophthalmic apparatus 100 according to this embodiment when viewed from above, and FIG. 1B is a diagram of the ophthalmic apparatus 100 according to this embodiment when viewed from the side.

As illustrated in FIG. 1A and FIG. 1B, the ophthalmic apparatus 100 according to this embodiment includes a head unit 110, a stage unit 120, a face receiving unit 130, a liquid crystal monitor 140, a control PC 150, and a joystick 160.

The head unit 110 is installed on the stage unit 120, and a main optical system is built in the head unit 110. The head unit 110 is moved in a horizontal direction by tilting the joystick 160 and in a vertical direction by rotating the joystick 160. The stage unit 120 moves the head unit 110 in the horizontal and vertical directions in response to the operation of the joystick 160. The face receiving unit 130 adjusts the position of a face of a subject. The face receiving unit 130 includes a jaw receiver 131 configured to receive a jaw and a jaw receiver drive unit 132 configured to move the jaw receiver 131 with an electric stage. The liquid crystal monitor 140 displays various operation screens, various pieces of information, and the like. The control PC 150 controls the operation of the ophthalmic apparatus 100 in an integrated manner and performs various pieces of processing. The joystick 160 is operated by an examiner and is configured to give an instruction of movement of the head unit 110 in the horizontal and vertical directions.

<Schematic configuration of optical system of head unit 110>

Figure 2A:
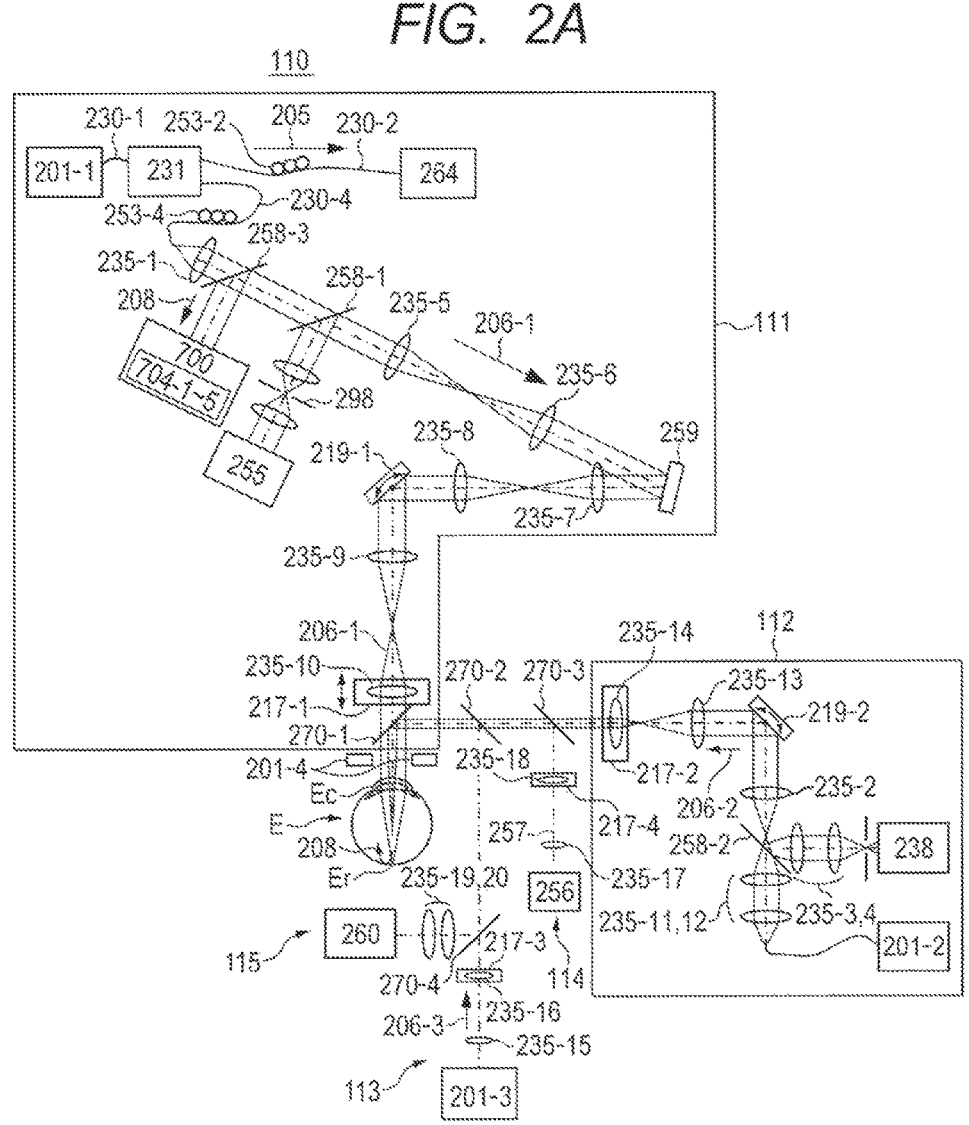
FIG. 2A is a diagram for illustrating an example of a schematic configuration of an optical system of a head unit illustrated in FIG. 1A and FIG. 1B.
Figure 2B:
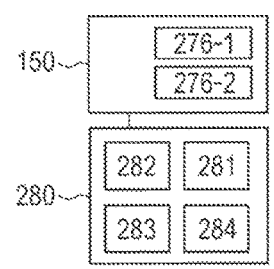
FIG. 2B is a diagram for illustrating an example of a configuration connected to a control PC illustrated in FIG. 1A and FIG. 1B.

FIG. 2A is a diagram for illustrating an example of a schematic configuration of the optical system of the head unit 110 illustrated in FIG. 1A and FIG. 1B, and FIG. 2B is a diagram for illustrating an example of a configuration connected to the control PC 150 illustrated in FIG. 1A and FIG. 1B.

As illustrated in FIG. 2A, the head unit 110 includes an AO-SLO apparatus 111, a WF-SLO apparatus 112, a beacon device 113, a fixation target display device 114, and an anterior ocular segment observation device 115.

Light emitted from a light source 201-1 is split into reference light 205 and measuring light 206-1 by an optical coupler 231. The measuring light 206-1 is guided into an eye to be inspected E that is an observation target through a single mode optical fiber 230-4, a spatial light modulator 259, an XY scanner 219-1, a dichroic mirror 270-1, and the like. Further, a light flux 257 from a fixation target 256 serves to prompt the eye to be inspected E to fixate or rotate.

The measuring light 206-1 is reflected or scattered by the eye to be inspected E so as to be return light 208, which travels an optical path in an opposite direction to enter detectors 704-1 to 704-5 through a beam splitter 258-3. The detectors 704-1 to 704-5 convert the light intensity of the return light 208 into a voltage signal, and an SLO image of the eye to be inspected E is formed through use of the voltage signal. In this embodiment, the entire optical system of the head unit 110 is mainly formed of a refracting optical system using lenses. However, it is also possible to form the optical system by using a reflecting optical system using spherical mirrors instead of the lenses. In addition, a reflective spatial light modulator is used as an aberration correction device in this embodiment, but it is also possible to use a transmissive spatial light modulator or a deformable mirror.

<<AO-SLO Apparatus 111>>

The AO-SLO apparatus 111 illustrated in FIG. 2A is now described.

First, details of the light source 201-1 are described below.

The light source 201-1 is, for example, a super luminescent diode (SLD) serving as a typical low-coherent light source. The light emitted from the light source 201-1 has a wavelength of about 840 nm and a bandwidth of about 50 nm. In this case, in order to acquire an SLO image having little speckle noise, a low-coherent light source is selected as the light source 201-1. Further, although the SLD is employed as the light source 201-1 in this embodiment, any type of light source may be used as long as the light source can emit low-coherent light. For example, an amplified spontaneous emission (ASE) light source may be used. Further, in view of the measurement of the eye to be inspected E, near infrared light is suitable as the light emitted from the light source 201-1. Further, the wavelength of the light emitted from the light source 201-1 affects the lateral resolution of the acquired SLO image, and hence the wavelength is desired to be as short as possible. Therefore, in this embodiment, the wavelength is set to about 840 nm. Note that, another wavelength may be selected depending on a measurement area of the observation target. The light emitted from the light source 201-1 is split into the reference light 205 and the measuring light 206-1 in a ratio of, for example, 90:10 by the optical coupler 231 through a single mode optical fiber 230-1. Further, polarization controllers 253-2 and 253-4 are respectively arranged on an optical fiber 230-2 and the single mode optical fiber 230-4.

Next, an optical path of the reference light 205 is described.

The reference light 205 obtained by the optical coupler 231 enters a light intensity measuring apparatus 264 through an optical fiber 230-2. The light intensity measuring apparatus 264 is used for measuring light intensity of the reference light 205 so as to monitor the light intensity of the measuring light 206-1.

Next, an optical path of the measuring light 206-1 is described.

The measuring light 206-1 obtained by the optical coupler 231 is guided to a lens 235-1 through the single mode optical fiber 230-4, and is adjusted to be a collimated light beam having a beam diameter of about 4 mm. The measuring light 206-1 passes through a beam splitter 258-1 and lenses 235-5 and 235-6 and enters the spatial light modulator 259. In this case, the spatial light modulator 259 is controlled by the control PC 150 via a spatial light modulator driver 281 included in a driver unit 280 illustrated in FIG. 2B. Next, the measuring light 206-1 is modulated by the spatial light modulator 259, passes through lenses 235-7 and 235-8, and enters a mirror of the XY scanner 219-1. For simplification of the illustration, the XY scanner 219-1 is illustrated in FIG. 2A as a single mirror. However, in an actual case, two mirrors, that is, an X scanner and a Y scanner, are disposed close to each other so as to raster-scan a retina Er in a direction perpendicular to the optical axis. The center of the measuring light 206-1 is adjusted to align with each center of rotation of the mirrors of the XY scanner 219-1.

The X scanner that is a component of the XY scanner 219-1 is a scanner configured to scan the measuring light 206-1 in a direction parallel to the drawing sheet, and a resonant scanner is used for the X scanner here. The drive frequency of the X scanner is approximately 7.9 kHz. In addition, the Y scanner that is a component of the XY scanner 219-1 is a scanner configured to scan the measuring light 206-1 in a direction perpendicular to the drawing sheet, and a galvano scanner is used for the Y scanner here. The drive waveform of the Y scanner is a sawtooth wave, the frequency thereof is approximately 32 Hz, and the duty ratio thereof is about 84%. The drive frequency of the Y scanner is an important parameter for determining a frame rate of the AO-SLO image photographed by the AO-SLO apparatus. The AO-SLO XY scanner 219-1 is controlled by the control PC 150 via an optical scanner driver 282 included in the driver unit 280 illustrated in FIG. 2B.

Lenses 235-9 and 235-10 correspond to an optical system configured to scan the retina Er, and serve to scan the retina Er with the measuring light 206-1 in a manner of pivoting on the center of a pupil of the eye to be inspected E. In this embodiment, the beam diameter of the measuring light 206-1 is about 4 mm, but the beam diameter may be larger than about 4 mm in order to acquire an image having higher resolution. Further, an electric stage 217-1 can move in a direction indicated by the arrows so as to move the position of the accompanying lens 235-10, to thereby perform focus adjustment. The electric stage 217-1 is controlled by the control PC 150 via an electric stage driver 283 included in the driver unit 280 illustrated in FIG. 2B.

The position of the lens 235-10 may be adjusted, to thereby focus the measuring light 206-1 to a predetermined layer of the retina Er of the eye to be inspected E to observe the layer. In addition, it is possible to support the case where the eye to be inspected E has ametropia. Further, in the ophthalmic apparatus 100 according to this embodiment, a confocal image and a nonconfocal image of the retina Er of a fundus of an eye can be photographed as described later. The lens 235-10 serving as a focus adjusting mechanism is a common optical path, and hence the focus position of the confocal image and that of the nonconfocal image are located at the same position.

Next, the measuring light 206-1 enters the eye to be inspected E and is reflected and scattered by the retina Er so as to be return light 208, which enters a photo-receiving unit 700. The return light 208 having entered the photo-receiving unit 700 is split by a beam splitter, and the split light beams reach detectors 704-1 to 704-5, respectively. As the detectors 704-1 to 704-5, for example, an avalanche photo diode (APD) or a photomultiplier tube (PMT) is used, which is a high speed sensor with high sensitivity.

Next, a schematic configuration of the photo-receiving unit 700 is described.

Figure 3:
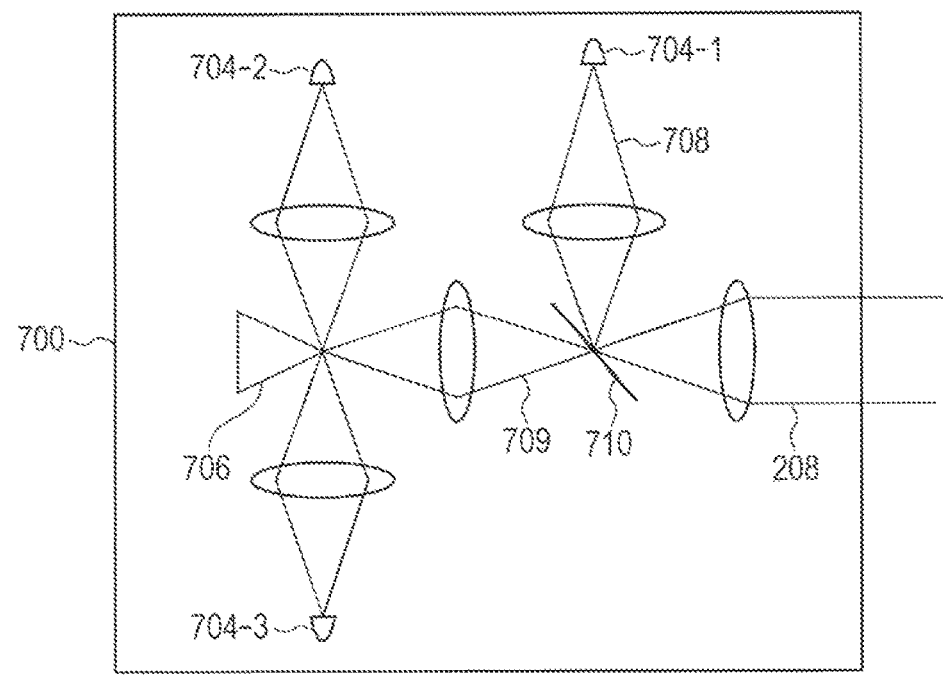
FIG. 3 is a diagram for illustrating an example of a schematic configuration of a photo-receiving unit illustrated in FIG. 2A.

FIG. 3 is a diagram for illustrating an example of a schematic configuration of the photo-receiving unit 700 illustrated in FIG. 2A.

As illustrated in FIG. 3, a part of the return light 208 entering a light shielding portion 710 arranged on an imaging surface is reflected to enter the detector 704-1. A schematic configuration of the light shielding portion 710 is described below with reference to FIG. 4.

Figure 4:
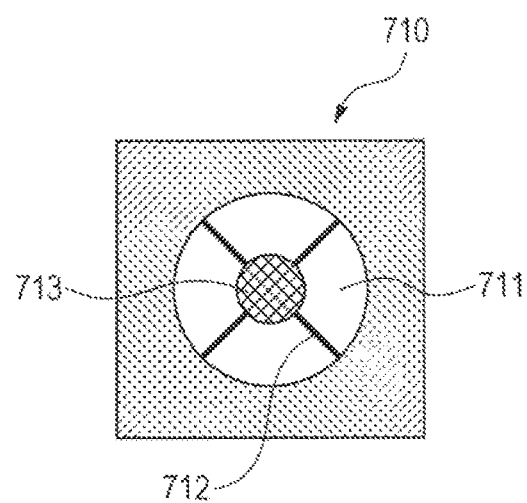
FIG. 4 is a diagram for illustrating an example of a schematic configuration of a light shielding portion illustrated in FIG. 3.

FIG. 4 is a diagram for illustrating an example of a schematic configuration of the light shielding portion 710 illustrated in FIG. 3.

Figure 5:
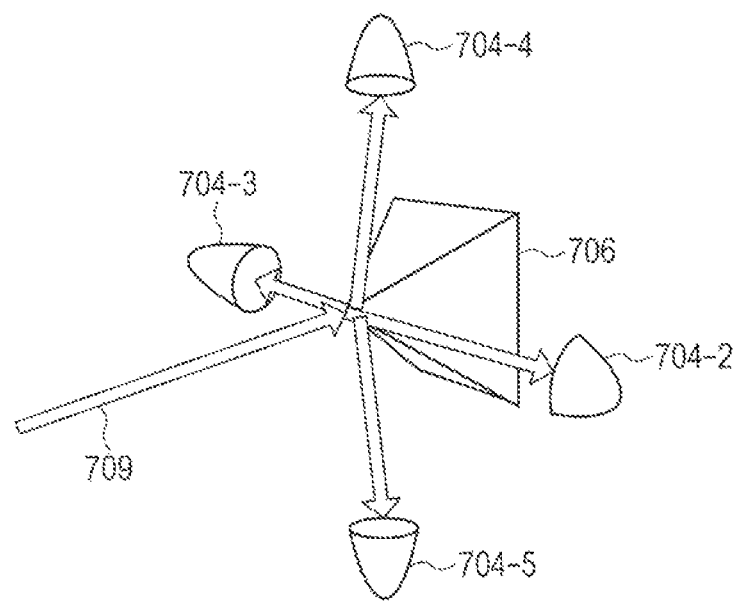
FIG. 5 is a diagram for illustrating an example of an arrangement relationship of detectors illustrated in FIG. 2A.

As illustrated in FIG. 4, the light shielding portion 710 includes a transmission region 711, a light shielding region 712, and a reflection region 713, and the center of the light shielding portion 710 is arranged so as to be positioned at the center of an optical axis of the return light 208. The light shielding portion 710 has an elliptical pattern that is formed into a circle when viewed from the optical axis direction when the light shielding portion 710 is arranged diagonally with respect to the optical axis of the return light 208. Light 708 reflected from the reflection region 713 of the light shielding portion 710 enters the detector 704-1 as illustrated in FIG. 3. In addition, as illustrated in FIG. 3, light 709 having passed through the transmission region 711 of the light shielding portion 710 is split by a quadrangular pyramid prism 706 arranged on the imaging surface, and the split light beams enter the detectors 704-2, 704-3, 704-4, and 704-5, respectively, as illustrated in FIG. 5. Note that, FIG. 5 is a diagram for illustrating an example of an arrangement relationship of the detectors 704-2, 704-3, 704-4, and 704-5 illustrated in FIG. 2A. In FIG. 5, the detectors 704-2 and 704-3 are arranged coaxially with a scanning direction of the X scanner of the XY scanner 219-1, and the detectors 704-4 and 704-5 are arranged coaxially with a scanning direction of the Y scanner of the XY scanner 219-1.

A voltage signal obtained by each of the detectors 704-1 to 704-5 is converted into a digital value by an AD board 276-1 included in the control PC 150, and then converted into an AO-SLO image that is a two-dimensional image by the control PC 150. Of those images, the AO-SLO image of the eye to be inspected E imaged based on the light 708 having entered the detector 704-1 becomes a confocal image focused within a particular narrow range. Further, the AO-SLO image of the eye to be inspected E imaged based on the light 709 input to the detectors 704-2 to 704-5 becomes a nonconfocal image focused within a wide range.

FIG. 10 is a diagram for illustrating a schematic structure of a photoreceptor cell of the eye to be inspected E according to the first embodiment of the present invention. As illustrated in FIG. 10, a photoreceptor cell 1000 includes a nucleus 1001, an inner segment 1002, and an outer segment 1003. Light having passed through a cornea Ec enters the photoreceptor cell 1000 from an upper portion as illustrated in FIG. 10. Further, in FIG. 10, a focus range (focal depth) 1010 to be photographed through use of the detector 704-1 and a focus range (focal depth) 1020 to be photographed through use of the detectors 704-2 to 704-5 are illustrated. As is understood from the focus ranges 1010 and 1020 illustrated in FIG. 10, the confocal image to be photographed through use of the detector 704-1 is an image within a narrow range in a focus direction compared to the nonconfocal image to be photographed through use of the detectors 704-2 to 704-5. When the focal point of the confocal image of the eye to be inspected E is aligned with the position of the outer segment 1003 as illustrated in FIG. 10, an image within the focus range 1010 of a part of the outer segment 1003 of the photoreceptor cell is photographed as the confocal image, and an image within the focus range 1020 including both the inner segment 1002 and the outer segment 1003 of the photoreceptor cell is photographed as the nonconfocal image.

<<WF-SLO Apparatus 112>>

The WF-SLO apparatus 112 illustrated in FIG. 2A is now described.

The WF-SLO apparatus 112 basically has the same configuration as that of the AO-SLO apparatus 111. Therefore, in the description of the WF-SLO apparatus 112, overlapping description of the same part as that of the AO-SLO apparatus 111 is omitted.

Light emitted from a light source 201-2 is guided to the eye to be inspected E that is an observation target through lenses 235-11 and 235-12, a lens 235-2, an XY scanner 219-2, lenses 235-13 and 235-14, dichroic mirrors 270-3 to 270-1, and the like. Similarly to the light source 201-1 of the AO-SLO apparatus 111, the light source 201-2 is an SLD. The light emitted from the light source 201-2 has a wavelength of about 920 nm and a bandwidth of about 20 nm.

Next, an optical path of measuring light 206-2 is described.

The measuring light 206-2 emitted from the light source 201-2 is guided to the eye to be inspected E through the lenses 235-11 and 235-12, the lens 235-2, the XY scanner 219-2, the lenses 235-13 and 235-14, the dichroic mirrors 270-3 to 270-1, and the like. An X-scanner that is a component of the XY scanner 219-2 is a scanner configured to scan the measuring light 206-2 in a direction parallel to the drawing sheet, and a resonant scanner is used for the X scanner here. The drive frequency of the X scanner is approximately 3.9 kHz. In addition, a Y scanner that is a component of the XY scanner 219-2 is a scanner configured to scan the measuring light 206-2 in a direction perpendicular to the drawing sheet, and a galvano scanner is used for the Y scanner here. The drive waveform of the Y scanner is a sawtooth wave, the frequency thereof is approximately 15 Hz, and the duty ratio thereof is about 84%. The drive frequency of the Y scanner is an important parameter for determining a frame rate of the WF-SLO image photographed by the WF-SLO apparatus 112. The beam diameter of the measuring light 206-2 is 1 mm, but may be larger than 1 mm in order to acquire an optical image with higher resolution. The measuring light 206-2 enters the eye to be inspected E and is reflected and scattered by the retina Er so as to be the return light 208, which reaches a detector 238 through the dichroic mirrors 270-1 to 270-3, the lenses 235-14 and 235-13, the XY scanner 219-2, the lenses 235-2 to 235-4, a beam splitter 258-2, and the like.

<<Beacon Device 113>>

Next, the beacon device 113 of FIG. 2A configured to measure an aberration occurred in the eye to be inspected E is described.

Measuring light 206-3 output from a light source 201-3 is guided to the eye to be inspected E that is the observation target through lenses 235-15 and 235-16, a dichroic mirror 270-4, and the like. In this case, the measuring light 206-3 enters the eye to be inspected E under a state of being decentered from the center of the eye to be inspected E in order to avoid being reflected from the cornea Ec. A part of the return light 208 based on the measuring light 206-3 enters a wavefront sensor 255 through the beam splitter 258-1 and a pinhole 298. In the wavefront sensor 255, the aberration of the return light 208 occurred in the eye to be inspected E is measured. In this case, the pinhole 298 is installed for the purpose of shielding unnecessary light other than the return light 208. The wavefront sensor 255 is electrically connected to the control PC 150. The wavefront sensor 255 is a Shack-Hartmann wavefront sensor, and the measurement range thereof is set to from −10 D to +5 D. The obtained aberration is expressed through use of the Zernike polynomials and indicates the aberration of the eye to be inspected E. The Zernike polynomials include the following terms: tilt, defocus, astigmatism, coma, trefoil, and the like. Note that, the measuring light 206-3 emitted from the light source 201-3 has a center wavelength of about 760 nm and a wavelength width of about 20 nm. In this case, the lenses 235-5 to 235-10 and the like are arranged so that the cornea Ec, the XY scanner 219-1, the wavefront sensor 255, and the spatial light modulator 259 are optically conjugate to each other. Therefore, the wavefront sensor 255 can measure the aberration of the eye to be inspected E. In addition, the spatial light modulator 259 can correct the aberration of the eye to be inspected E.

<<Fixation Target Display Device 114>>

The fixation target 256 is formed of a light-emitting display module and has a display surface (27 mm×27 mm, 128 pixels×128 pixels) on an XY-plane. In this case, a liquid crystal, an organic EL, an LED array, or the like can be used as the display surface. When the eye to be inspected E watches the light flux 257 from the fixation target 256, the eye to be inspected E is prompted to fixate or rotate.

Figure 6:
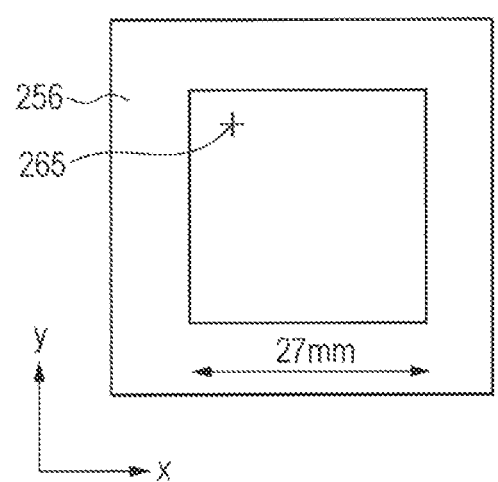
FIG. 6 is a diagram for illustrating an example of a display surface of a fixation target illustrated in FIG. 2A.

FIG. 6 is a diagram for illustrating an example of the display surface of the fixation target 256 illustrated in FIG. 2A.

On the display surface of the fixation target 256, for example, a cross-shaped pattern is displayed so as to blink at any lighting position 265 as illustrated in FIG. 6. The light flux 257 from the fixation target 256 is guided to the retina Er through lenses 235-17 and 235-18, the dichroic mirrors 270-3 to 270-1, and the like. Further, the lenses 235-17 and 235-18 are arranged so that the display surface of the fixation target 256 and the retina Er are optically conjugate to each other. Further, the fixation target 256 is controlled by the control PC 150 via a fixation target driver 284 included in the driver unit 280.

<<Anterior Ocular Segment Observation Device 115>>

Next, the anterior ocular segment observation device 115 illustrated in FIG. 2A is described.

Light emitted from an anterior ocular segment illumination light source 201-4 illuminates the eye to be inspected E. The light reflected from the eye to be inspected E enters a CCD camera 260 through the dichroic mirrors 270-1, 270-2, and 270-4, and lenses 235-19 and 235-20. The anterior ocular segment illumination light source 201-4 is, for example, an LED configured to emit light having a center wavelength of about 740 nm.

<<Focus, Shutter, and Astigmatism Correction>>

As described above, the head unit 110 includes the optical system including the AO-SLO apparatus 111, the WF-SLO apparatus 112, the beacon device 113, the fixation target display device 114, and the anterior ocular segment observation device 115. Of those, the AO-SLO apparatus 111, the WF-SLO apparatus 112, the beacon device 113, and the fixation target display device 114 have the electric stages 217-1 to 217-4, respectively and individually, and through the coordinated movement of the four electric stages 217-1 to 217-4, the focus is adjusted. Note that, in the case where a focus position is intended to be adjusted individually, the focus position can be adjusted individually by moving the electric stage individually.

Further, the AO-SLO apparatus 111, the WF-SLO apparatus 112, and the beacon device 113 each include a shutter (not shown), and whether or not the light is caused to enter the eye to be inspected E can be controlled individually by opening or closing the shutter. Note that, the shutter is used here, but whether or not the light is caused to enter the eye to be inspected E can also be controlled by directly turning on/off the light sources 201-1 to 201-3. Similarly, the anterior ocular segment observation device 115 and the fixation target display device 114 can also be controlled by turning on/off the anterior ocular segment illumination light source 201-4 and the fixation target 256. Further, the lens 235-10 can be replaced, and a spherical lens or a cylindrical lens may be used in accordance with the aberration (ametropia) of the eye to be inspected E. Further, the number of the lenses is not limited to one, and a plurality of lenses may be combined and installed.

<<Wavelength>>

Figure 7:
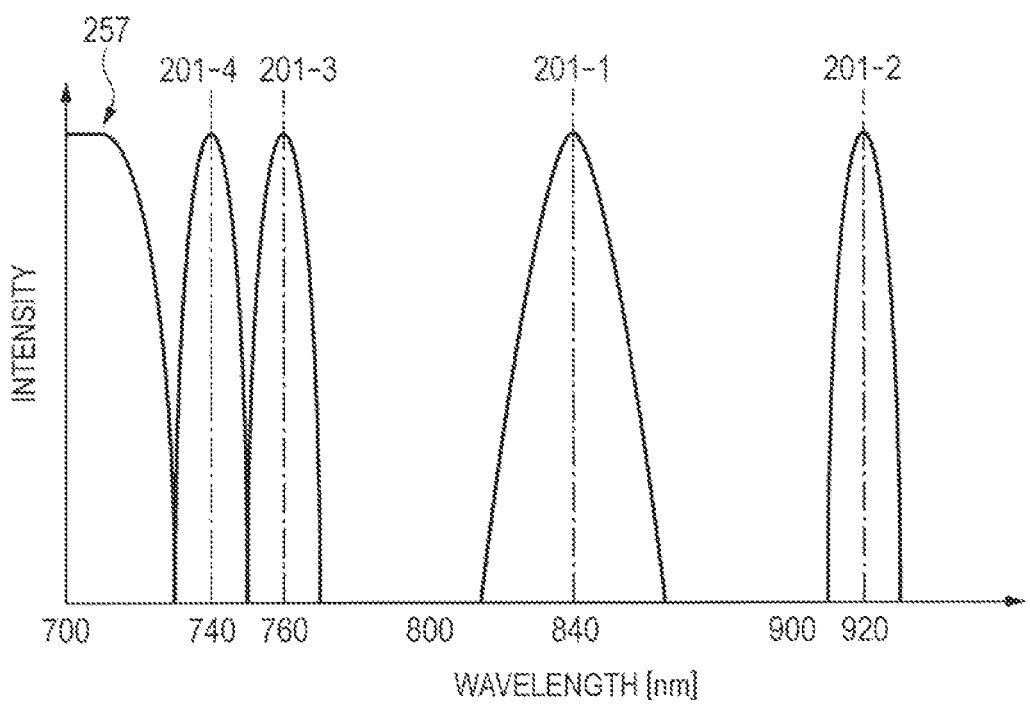
FIG. 7 is a graph for showing a wavelength distribution of each light source used in an AO-SLO apparatus, a WF-SLO apparatus, a beacon device, a fixation target display device, and an anterior ocular segment observation device illustrated in FIG. 2A.

FIG. 7 is a graph for showing the wavelength distribution of each of the light sources used in the AO-SLO apparatus 111, the WF-SLO apparatus 112, the beacon device 113, the fixation target display device 114, and the anterior ocular segment observation device 115 illustrated in FIG. 2A. In this embodiment, in order to separate the light beams by the dichroic mirrors 270-1 to 270-4, the light beams are set to have different wavelength bands. Note that, the difference in wavelength of the respective light sources is shown in FIG. 7, and the intensity and spectrum shape thereof are not defined therein.

<Imaging by Control PC 150>

Next, an imaging method performed by the control PC 150 is described.

The light that has entered one of the detectors 704-1 to 704-5 is subjected to photoelectric conversion in the one of the detectors 704-1 to 704-5 and is converted into a digital value by the AD board 276-1 included in the control PC 150. In the control PC 150, the digital value is further subjected to data processing synchronized with the operation and drive frequency of the XY scanner 219-1, to thereby form an AO-SLO image. An AO-SLO image formed based on the light having entered the detector 704-1, that is, the light 708 reflected from the reflection region 713 in the light shielding portion 710 corresponding to a pinhole, is a confocal image. Meanwhile, an AO-SLO image formed based on the light having entered the detectors 704-2 to 704-5, that is, the scattering light 709 having passed through the transmission region 711 on the periphery of the reflection region 713 in the light shielding portion 710 corresponding to the pinhole, is a nonconfocal image. The detectors 704-1 to 704-5 and the control PC 150 configured to perform processing of photographing the confocal image and the nonconfocal image form an acquisition unit.

Digital values obtained from light beams at certain time when the light beams enter the detectors 704-2, 704-3, 704-4, and 704-5 are respectively defined as Ia, Ib, Ic, and Id. Then, differential values I' and I'' in the X-direction and the Y-direction can be determined based on Expressions (1) and (2).

$$I'=(Ia-Ib)/(Ia+Ib) \quad (1)$$

$$I''=(Ic-Id)/(Ic+Id) \quad (2)$$

Through use of an image value occurred with the differential values I' and I'' in the X-direction and the Y-direction, an image with an outline emphasized can be acquired. Further, as the configuration of the photo-receiving unit 700, the configuration is described in which the number of the detectors is set to four to acquire the digital values Ia, Ib, Ic, and Id. However, another configuration may be considered. For example, there may be adopted a configuration in which two detectors are arranged so as to be line-symmetric with respect to a branched point of the quadrangular pyramid prism, and a drive unit configured to rotate the branched direction of the quadrangular pyramid prism and the two detectors around the branched point is provided. In the case of this configuration, when the quadrangular pyramid prism and the detectors are rotated around the optical axis of the light 709, the information on the differential value I' and the rotation angle can be acquired.

Similarly, in the WF-SLO apparatus 112, a voltage signal obtained by the WF-SLO detector 238 is converted into a digital value by the AD board 276-2 included in the control PC 150, to thereby form a WF-SLO image.

<Processing Procedure in Control Method for Ophthalmic Apparatus 100>

Next, a processing procedure in a control method for the ophthalmic apparatus 100 according to this embodiment is described.

Figure 8:
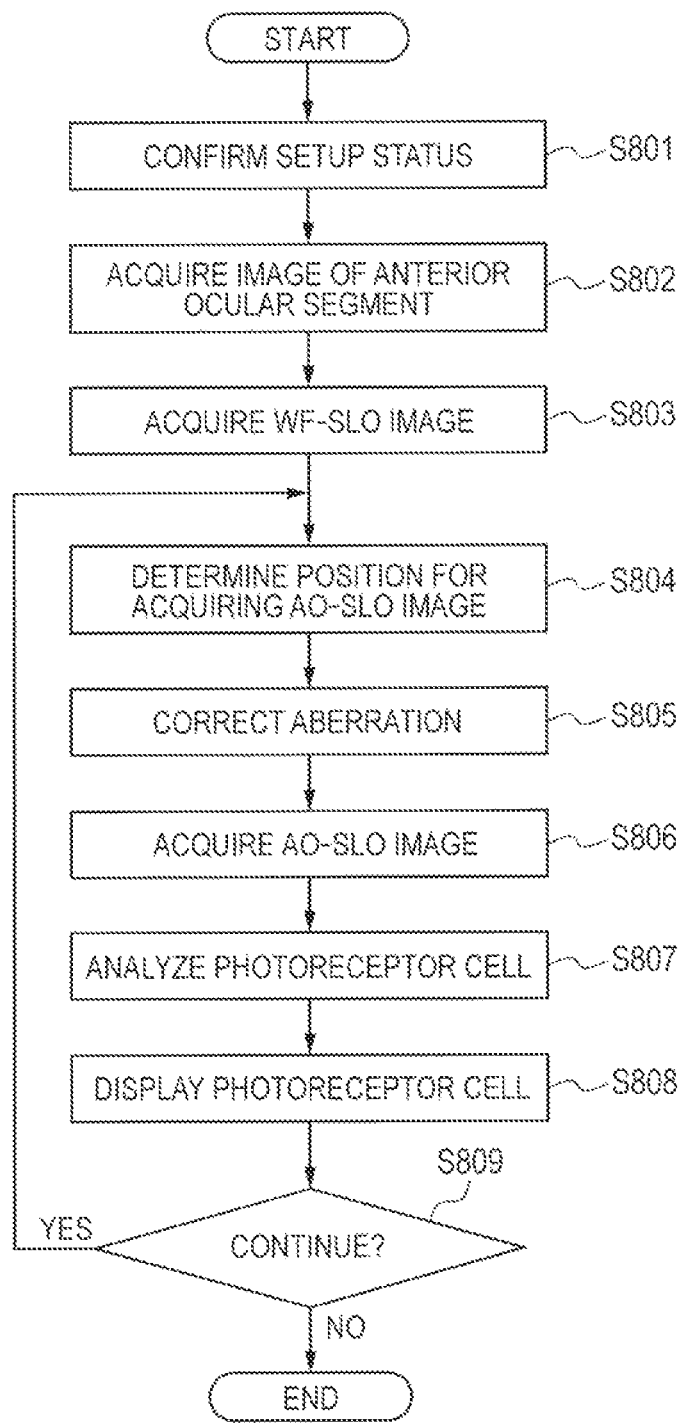
FIG. 8 is a flowchart for illustrating an example of a processing procedure in a control method for an ophthalmic apparatus according to the first embodiment of the present invention.
Figure 9:
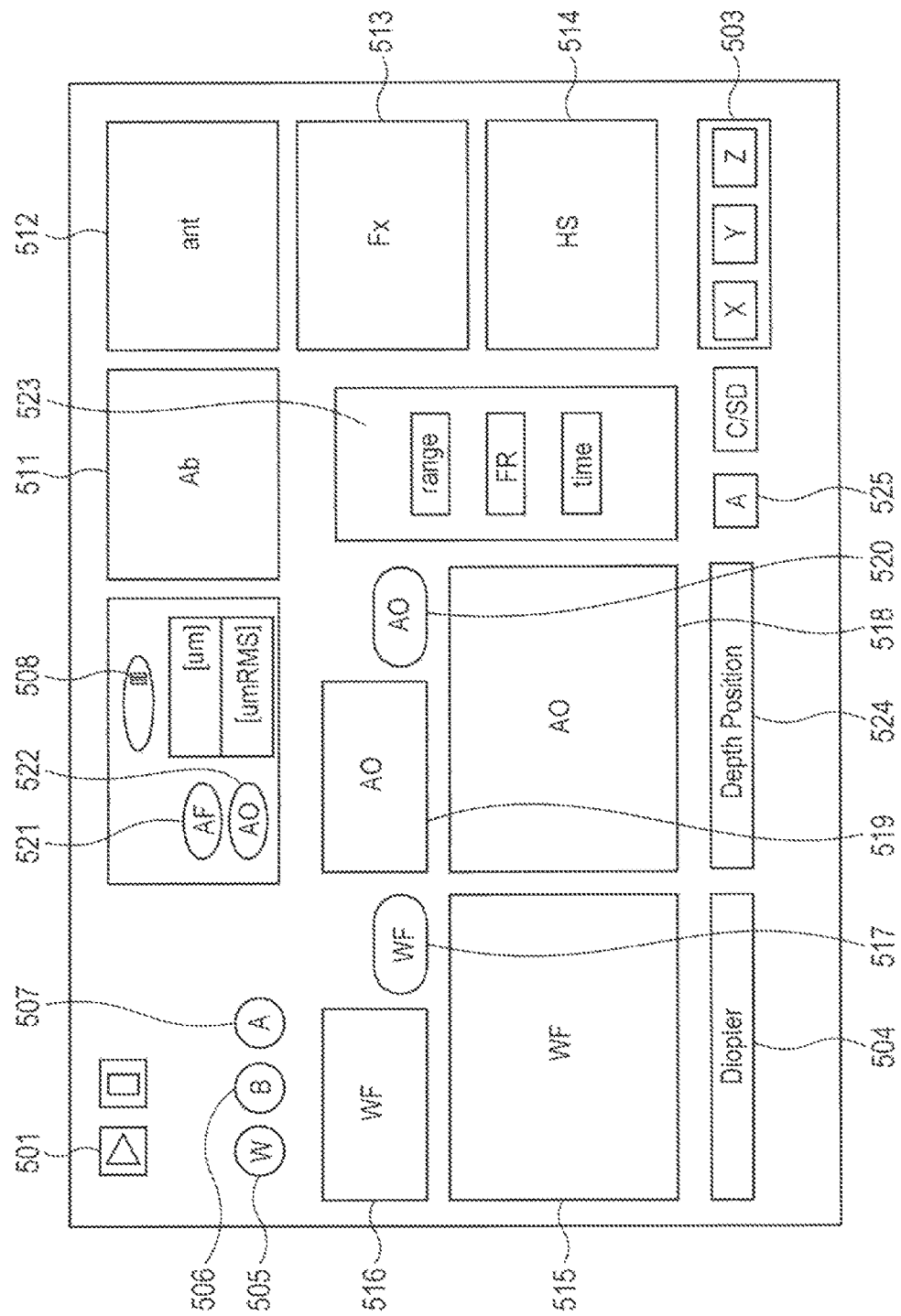
FIG. 9 is a diagram for illustrating an example of a control software screen to be used in the control method for an ophthalmic apparatus according to the first embodiment of the present invention.
Figure 11A:
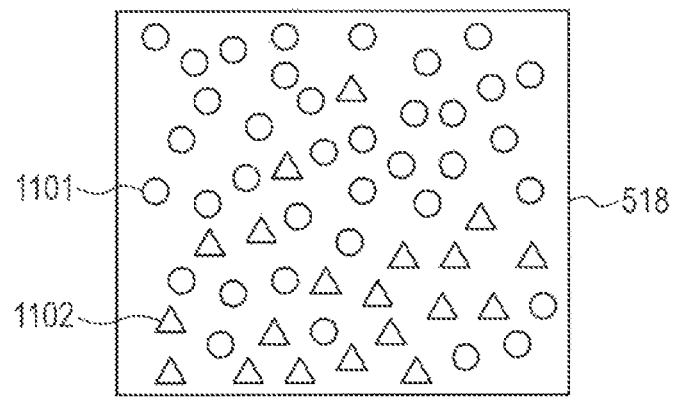
FIG. 11A, FIG. 11B and FIG. 11C are each a diagram for illustrating an example of a result of image processing in the control method for an ophthalmic apparatus according to embodiments of the present invention.
Figure 11B:
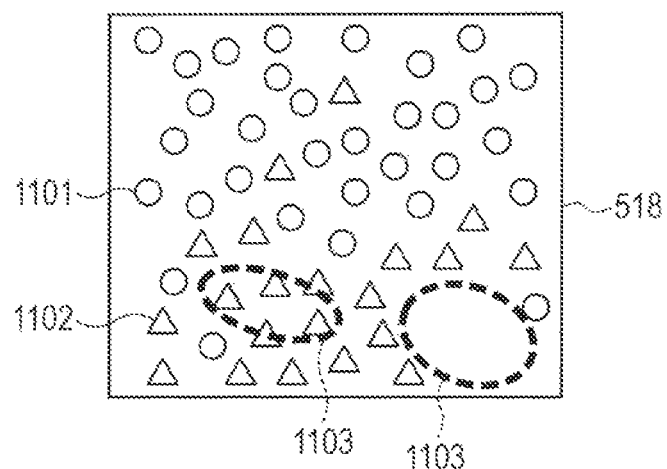
Figure 11C:
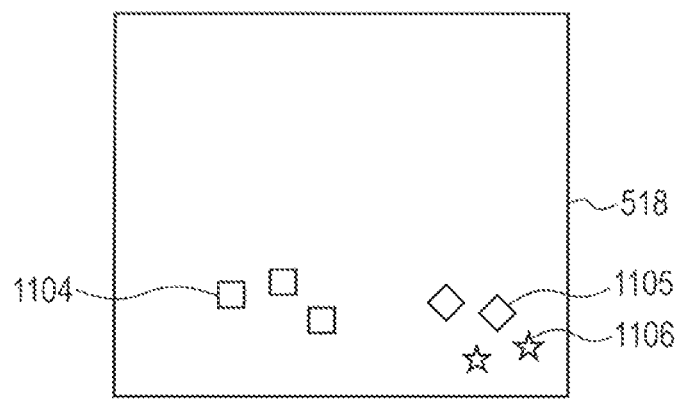

FIG. 8 is a flowchart for illustrating an example of the processing procedure in the control method for the ophthalmic apparatus 100 according to the first embodiment of the present invention. Further, FIG. 9 is a diagram for illustrating an example of a control software screen to be used in the control method for the ophthalmic apparatus 100 according to the first embodiment of the present invention. Further, FIG. 11A to FIG. 11C are each a diagram for illustrating an example of a result of image processing in the control method for the ophthalmic apparatus 100 according to embodiments of the present invention. The flowchart illustrated in FIG. 8 is described through use of the configuration illustrated in FIG. 2A and FIG. 2B, the control software screen illustrated in FIG. 9, and the result of the image processing illustrated in FIG. 11A, as necessary.

<<S801: Confirmation of Setup Status>>

When an examiner turns on the power of the ophthalmic apparatus 100, in Step S801, the control PC 150 confirms the setup status of the ophthalmic apparatus 100. Then, the control PC 150 activates control software to display the control software screen illustrated in FIG. 9 on the liquid crystal monitor 140. At this time, a subject puts his or her face on the face receiving unit 130.

<<S802: Acquisition of Image of Anterior Ocular Segment>>

For example, when the examiner presses an execution button 501 on the control software screen displayed on the liquid crystal monitor 140, in Step S802, the control PC 150 photographs an anterior ocular segment of the eye to be inspected E through use of the anterior ocular segment observation device 115, to thereby acquire an image of the anterior ocular segment. Then, the control PC 150 displays the acquired image of the anterior ocular segment on an anterior ocular segment image display monitor 512 illustrated in FIG. 9. Specifically, the image of the anterior ocular segment is photographed by the CCD camera 260. In the case where the center of a pupil of the eye to be inspected E is not correctly displayed at the center of the screen of the anterior ocular segment image display monitor 512 illustrated in FIG. 9, the examiner first moves the head unit 110 to a substantially correct position through use of the joystick 160. In the case where further adjustment is required, the examiner presses an electric stage button 503 on the control software screen illustrated in FIG. 9 to slightly move the jaw receiver drive unit 132.

<<S803: Acquisition of WF-SLO Image>>

Then, in Step S803, when the examiner presses a WF-SLO measurement button 505, the control PC 150 photographs the retina Er of the eye to be inspected E through use of the WF-SLO apparatus 112, to thereby acquire a WF-SLO image. In this step, the control PC 150 can adjust the scanning width of the XY scanner 219-2, to thereby photograph the retina Er of the fundus of the eye of the subject with a size of 8 mm×6 mm. In the case where the image of the anterior ocular segment is displayed in a substantially correct state, the acquired WF-SLO image is displayed on a WF-SLO image display monitor 515 illustrated in FIG. 9. At this time, the examiner sets the fixation target 256 at a center position with a fixation target position display monitor 513 to guide the line of sight of the eye to be inspected E to the center. Next, the examiner adjusts a focus adjustment button 504 so as to increase signal intensity of the WF-SLO image while watching a WF-SLO intensity monitor 516 illustrated in FIG. 9. On the WF-SLO intensity monitor 516, signal intensity detected by the WF-SLO apparatus 112 is displayed in a time series, with the horizontal axis being time and the vertical axis being the signal intensity of the WF-SLO image. Then, through adjustment of the focus adjustment button 504 illustrated in FIG. 9, the positions of the lenses 235-10, 235-14, 235-16, and 235-18 are adjusted concurrently. In the case where the WF-SLO image is displayed clearly on the WF-SLO image display monitor 515 illustrated in FIG. 9, the examiner presses a WF-SLO image recording button 517 to acquire and save the WF-SLO image.

<<S804: Determination of Position for Acquiring AO-SLO Image>>

When the examiner confirms the WF-SLO image displayed on the WF-SLO image display monitor 515 illustrated in FIG. 9 and determines a position at which an AO-SLO image is intended to be acquired through use of a procedure described later, in Step S804, the control PC 150 determines the above-mentioned position as a position for acquiring an AO-SLO image. Then, the control PC 150 guides the line of sight of the eye to be inspected E so that the position for acquiring an AO-SLO image is placed at the center of the WF-SLO image display monitor 515. Herein, there are two methods of determining the position for acquiring an AO-SLO image. One of the methods is a method involving designating the position of the fixation target 256 in the fixation target position display monitor 513, and the other is a method involving clicking on an intended position on the WF-SLO image display monitor 515. In this embodiment, pixels on the WF-SLO image display monitor 515 are associated with the position of the fixation target 256 so that the position of the fixation target 256 can move automatically to guide the line of sight of the eye to be inspected E to an intended position. Then, the examiner confirms that the position for acquiring an AO-SLO image has moved to the center of the WF-SLO image display monitor 515, and then the flow shifts to the subsequent step.

<<S805: Aberration Correction>>

When the examiner presses an aberration measurement button 506 illustrated in FIG. 9, in Step S805, the control PC 150 first blocks the measuring light 206-2 to be used in the WF-SLO apparatus 112 and opens the shutter (not shown) of the beacon device 113, to thereby irradiate the eye to be inspected E with the measuring light 206-3 serving as beacon light. With this, a Hartmann image detected by the wavefront sensor 255 is displayed on a wavefront sensor monitor 514 illustrated in FIG. 9. Then, the control PC 150 displays an aberration calculated based on the Hartmann image on an aberration correction monitor 511. At this time, the aberration is displayed so as to be separated into a defocus component (unit: μm) and the entire aberration amount (unit: μmRMS). In this case, the positions of the focusing lens 235-10 for the measuring light 206-1 and the focusing lens 235-16 for the measuring light 206-3 are adjusted in Step 803, and hence aberration measurement is ready to be performed in this step.

Specifically, the return light 208 with respect to the measuring light 206-3 passes through the pinhole 298 without being blocked and is in a state of reaching the wavefront sensor 255. In this case, when the examiner presses an automatic focus button 521 illustrated in FIG. 9, the control PC 150 automatically adjusts the positions of the lenses 235-10, 235-14, 235-16, and 235-18 so that the value of defocus decreases. Next, when the examiner presses an aberration correction button 522 illustrated in FIG. 9, the control PC 150 automatically adjusts the spatial light modulator 259 so that the aberration amount decreases, and displays the value of the aberration amount in real time. In this case, when the value of the aberration amount reaches a threshold value (for example, 0.03 μmRMS) or less determined in advance, an AO-SLO measurement button 507 is automatically pressed, and the flow shifts to the subsequent step. The threshold value of the aberration amount can be set arbitrarily. Further, in the case where the value of the aberration amount does not reach the threshold value or less, the examiner presses an aberration correction temporary stop button 508 to stop the aberration correction. After that, the examiner presses the AO-SLO measurement button 507 to cause the flow to shift to the subsequent step.

<<S806: Acquisition of AO-SLO Image>>

In the ophthalmic apparatus 100 according to this embodiment, a photographing field angle, a frame rate, and a photographing time can be designated by pressing photographing condition setting buttons 523 illustrated in FIG. 9. The photographing field angle can be adjusted by controlling the scan width of the XY scanner 219-1. In this embodiment, the retina Er of the fundus of the eye of the subject is photographed with a size of 200 μm×200 μm and a resolution of 400 pixels×400 pixels.

When the examiner presses the AO-SLO measurement button 507 illustrated in FIG. 9, in Step S806, the control PC 150 first blocks the measuring light 206-3 serving as the beacon light and opens the shutter of the measuring light 206-1, to thereby irradiate the eye to be inspected E with the measuring light 206-1. Then, the control PC 150 photographs the retina Er of the eye to be inspected E through use of the AO-SLO apparatus 111, to thereby acquire an AO-SLO image. Then, the control PC 150 displays the AO-SLO image having the aberration corrected on an AO-SLO image display monitor 518. The AO-SLO image thus displayed is a confocal image based on the signal detected by the detector 704-1. Note that, in this step, the control PC 150 also acquires a nonconfocal image that is an AO-SLO image based on the signals detected by the detectors 704-2 to 704-5 in addition to the confocal image that is the AO-ALO image based on the signal detected by the detector 704-1. Further, the control PC 150 displays signal intensity detected by the AO-SLO apparatus 111 in a time series on an AO-SLO intensity monitor 519 illustrated in FIG. 9, similarly to the WF-SLO intensity monitor 516. In the case where the signal intensity is insufficient, the examiner adjusts the position of the face receiving unit 130 while watching the AO-SLO intensity monitor 519 so that the signal intensity increases.

Further, the examiner can move the lens 235-10 through adjustment of a depth adjustment button 524 illustrated in FIG. 9, to thereby adjust the photographing position in the depth direction of the eye to be inspected E. Specifically, the examiner confirms the confocal image displayed on the AO-SLO image display monitor 518 and adjusts a focus position to a position at which a photoreceptor cell of the retina Er of the fundus of the eye is clearly seen, here, adjusts the focus position so that the outer segment 1003 of the photoreceptor cell is in focus. In the case where a tomographic image of the fundus of the eye to be inspected E is photographed in advance by an optical coherence tomography (OTC) apparatus, the focus position of the photoreceptor cell may be adjusted to the outer segment 1003 of the photoreceptor cell through use of tomographic information on the fundus of the eye.

In the case where the AO-SLO image is clearly displayed, the examiner presses an AO-SLO recording button 520, and the control PC 150 saves the AO-SLO image acquired by photographing. Then, the control PC 150 blocks the measuring light 206-1. Here, in the control PC 150, as described above, a confocal image is formed based on the light 708 having entered the detector 704-1 and a nonconfocal image is formed based on the light 709 having entered the detectors 704-2 to 704-5. In this case, the nonconfocal image is formed through use of the differential value I' in the X-direction described in the section of imaging.

<<S807: Photoreceptor Cell Analysis>>

Then, when the examiner presses a photoreceptor cell analysis button 525 illustrated in FIG. 9, in Step S807, the control PC 150 detects the photoreceptor cells based on known image processing with respect to the confocal image and the nonconfocal image of the AO-SLO image acquired in Step S806. In this case, as described above, the confocal image is an image within the range 1010 of a part of the outer segment 1003 of the photoreceptor cell, and the nonconfocal image is an image within the range 1020 including both the inner segment 1002 and the outer segment 1003 of the photoreceptor cell.

Then, in this step, specifically, the control PC 150 detects the photoreceptor cell of the eye to be inspected E through use of the confocal image. More specifically, the control PC 150 detects the outer segment 1003 of the photoreceptor cell of the eye to be inspected E through use of the confocal image. The control PC 150 configured to detect the photoreceptor cell (more specifically, the outer segment 1003 of the photoreceptor cell) of the eye to be inspected E through use of the confocal image forms a first detection unit.

Further, in this step, specifically, the control PC 150 detects the photoreceptor cell of the eye to be inspected E through use of the nonconfocal image. More specifically, the control PC 150 detects the inner segment 1002 and the outer segment 1003 of the photoreceptor cell of the eye to be inspected E through use of the nonconfocal image. The control PC 150 configured to detect the photoreceptor cell (more specifically, the inner segment 1002 and the outer segment 1003 of the photoreceptor cell) of the eye to be inspected E through use of the nonconfocal image forms a second detection unit.

<<S808: Display of Photoreceptor Cell>>

Then, in Step S808, the control PC 150 first compares the photoreceptor cell of the eye to be inspected E detected through use of the confocal image and the photoreceptor cell of the eye to be inspected E detected through use of the nonconfocal image with each other. The control PC 150 configured to perform this comparison forms a comparison unit. Then, the control PC 150 displays a result of the comparison on the control software screen (specifically, the AO-SLO image display monitor 518) illustrated in FIG. 9. The control PC 150 configured to perform this display forms a display unit.

FIG. 11A is a diagram for illustrating an example of the result of the comparison between the photoreceptor cell of the eye to be inspected E detected through use of the confocal image and the photoreceptor cell of the eye to be inspected E detected through use of the nonconfocal image, which is displayed on the AO-SLO image display monitor 518. In FIG. 11A, a photoreceptor cell 1101 indicates a photoreceptor cell that is detected from both the confocal image and the nonconfocal image. Further, a photoreceptor cell 1102 indicates a photoreceptor cell that is detected from the nonconfocal image but is not detected from the confocal image. As described above, the confocal image is acquired by photographing the outer segment 1003 of the photoreceptor cell, and the nonconfocal image is acquired by photographing both the inner segment 1002 and the outer segment 1003 of the photoreceptor cell. That is, in FIG. 11A, the photoreceptor cell 1101 indicates a photoreceptor cell in which both the inner segment 1002 and the outer segment 1003 are in a healthy state, and the photoreceptor cell 1102 indicates a photoreceptor cell in which the inner segment 1002 is in a healthy state but the outer segment 1003 has a failure. In general, regarding a failure of the photoreceptor cell, the outer segment 1003 of the photoreceptor cell is lost in an initial stage, and the inner segment 1002 is also lost along with the progress of the failure.

That is, in this step, based on the detection result of the outer segment 1003 of the photoreceptor cell obtained through use of the confocal image and the detection result of the inner segment 1002 and the outer segment 1003 of the photoreceptor cell obtained through use of the nonconfocal image, the state of each photoreceptor cell of the eye to be inspected E is displayed. Further, in this step, the detection result of the photoreceptor cell obtained through use of the confocal image and the detection result of the photoreceptor cell obtained through use of the nonconfocal image are displayed on the same screen (AO-SLO image display monitor 518).

<<S809: Determination of Photographing Continuation>>

Then, in Step S809, the control PC 150 determines whether or not photographing of the eye to be inspected E is to be continued based on, for example, an operation instruction from the examiner. As a result of this determination, in the case where photographing of the eye to be inspected E is to be continued (S809/Yes), the flow returns to Step S804, and the processing of Step S804 and the subsequent steps is performed again.

Meanwhile, as a result of the determination in Step S809, in the case where photographing of the eye to be inspected E is not to be continued (S809/No), the result of the comparison is saved in a storage unit (not shown) together with the information specifying the eye to be inspected, information on the photographing position, and each image, and the processing of the flowchart illustrated in FIG. 8 is ended.

According to this embodiment, the result of the comparison between the photoreceptor cell detected through use of the confocal image and the photoreceptor cell detected through use of the nonconfocal image is displayed, and hence the detailed state of the photoreceptor cell of the eye to be inspected E can be grasped.

More specifically, the confocal image has a feature in that the state within a narrow range in a focus direction including the inner segment 1002 or the outer segment 1003 of the photoreceptor cell is observed easily, and the nonconfocal image has a feature in that the state within a wide range in the focus direction including a combination of the inner segment 1002 and the outer segment 1003 of the photoreceptor cell is observed easily. Therefore, according to this embodiment, it is possible to grasp the degree of a failure of the photoreceptor cell in more detail.

Second Embodiment

Next, a second embodiment of the present invention is described. Note that, in the following description of the second embodiment, the description of the same processing contents as those of the first embodiment described above is omitted, and processing contents different from those of the first embodiment described above are described.

As described above, FIG. 11A to FIG. 11C are each a diagram for illustrating an example of the result of image processing in the control method for the ophthalmic apparatus 100 according to the embodiments of the present invention.

In the second embodiment, the control PC 150 first performs the processing of the flowchart illustrated in FIG. 8 at a certain point of time (first time). Then, the control PC 150 obtains the result of the comparison (first comparison result) between the photoreceptor cell detected through use of the confocal image and the photoreceptor cell detected through use of the nonconfocal image, which is illustrated in FIG. 11A. The control PC 150 configured to obtain the result of the comparison between the photoreceptor cell detected through use of the confocal image and the photoreceptor cell detected through use of the nonconfocal image forms a first comparison unit.

Then, at a point of time (second time) after, for example, 3 months have elapsed from the time when the result of FIG. 11A was obtained, the control PC 150 performs the processing of the flowchart illustrated in FIG. 8 with respect to the same photographing region as that of the same eye to be inspected E based on the positional information and the like saved in the storage unit. Then, the control PC 150 obtains a result of the comparison (second comparison result) between the photoreceptor cell detected through use of the confocal image and the photoreceptor cell detected through use of the nonconfocal image, which is illustrated in FIG. 11B. Specifically, in FIG. 11B, the photoreceptor cell 1101 indicates a photoreceptor cell in which both the inner segment 1002 and the outer segment 1003 are in a healthy state, and the photoreceptor cell 1102 indicates a photoreceptor cell in which the inner segment 1002 is in a healthy state but the outer segment 1003 has a failure. Then, in FIG. 11B, regions in which the states of the photoreceptor cells changed with respect to FIG. 11A are illustrated as regions 1103.

Then, in the second embodiment, the control PC 150 compares the first comparison result obtained at the first time illustrated in FIG. 11A and the second comparison result obtained at the second time illustrated in FIG. 11B. The control PC 150 configured to compare the first comparison result and the second comparison result obtained at different times forms a second comparison unit. Then, the control PC 150 further displays the result of this comparison on the AO-SLO image display monitor 518. The state of this display is illustrated in FIG. 11C.

In FIG. 11C, a photoreceptor cell 1104 indicates a photoreceptor cell that can be detected in both the confocal image and the nonconfocal image at the first time illustrated in FIG. 11A, but can be detected only in the nonconfocal image at the second time illustrated in FIG. 11B. That is, the photoreceptor cell 1104 indicates a photoreceptor cell which was in a healthy state 3 months ago (at the first time illustrated in FIG. 11A), but in which the inner segment 1002 is in a healthy state but the outer segment 1003 has a failure at the current time (at the second time illustrated in FIG. 11B).

In FIG. 11C, a photoreceptor cell 1105 indicates a photoreceptor cell that cannot be detected from the confocal image but can be detected from the nonconfocal image at the first time illustrated in FIG. 11A, but cannot be detected from the confocal image or the nonconfocal image at the second time illustrated in FIG. 11B. That is, the photoreceptor cell 1105 indicates a photoreceptor cell in which the outer segment 1003 had a failure but the inner segment 102 was in a healthy state 3 months ago (at the first time illustrated in FIG. 11A), but in which the inner segment 1002 also has a failure at the current time (at the second time illustrated in FIG. 11B).

In FIG. 11C, a photoreceptor cell 1106 indicates a photoreceptor cell that can be detected from both the confocal image and the nonconfocal image at the first time illustrated in FIG. 11A, but cannot be detected from the confocal image or the nonconfocal image at the second time illustrated in FIG. 11B. That is, the photoreceptor cell 1106 indicates a photoreceptor cell in which both the outer segment 1003 and the inner segment 1002 were in a healthy state 3 months ago (at the first time illustrated in FIG. 11A), but in which both the outer segment 1003 and the inner segment 1002 have a failure at the current time (at the second time illustrated in FIG. 11B).

According to this embodiment, through periodical observation of the state of the photoreceptor cell in the same region of the eye to be inspected E, the degree of progress of a failure of the photoreceptor cell can be easily grasped.

Other Embodiments

In the above-mentioned first and second embodiments, in FIG. 11A to FIG. 11C, the states of the photoreceptor cells are described through use of a method of discriminating the states with symbols such as "○" and "Δ", but the states of the photoreceptor cells may be displayed by other methods. For example, the mode of displaying the photoreceptor cells through use of a method capable of discriminating the states of the photoreceptor cells for each group with a color or a combination of a color and a shape instead of the symbols is also applicable to the present invention.

Further, in the above-mentioned first and second embodiments, the method of displaying only symbols indicating the states of the photoreceptor cells on the AO-SLO image display monitor 518 is described. However, the present invention is not limited thereto. For example, the mode of displaying the confocal image or the nonconfocal image on the AO-SLO image display monitor 518 and displaying symbols indicating the states of the photoreceptor cells and the like on the image in a superimposed manner is also applicable to the present invention.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-051045, filed Mar. 13, 2015, which is hereby incorporated by reference herein in its entirety.

What is claimed is:

1. An ophthalmic apparatus, comprising:
an acquisition unit configured to acquire a confocal image and a nonconfocal image of an eye to be inspected based on a return light from the eye to be inspected, wherein the confocal image is generated from a beam of a central part of the return light and the nonconfocal image is generated from a beam of a surround part surrounding the central part of the return light;
a first detection unit configured to detect a plurality of photoreceptor cells of the eye to be inspected from the confocal image, wherein the first detection unit detects a plurality of outer segments of photoreceptor cells;
a second detection unit configured to detect a plurality of photoreceptor cells of the eye to be inspected from the nonconfocal image, wherein the second detection unit detects a plurality of inner segments and outer segments of photoreceptor cells;
a first comparison unit configured to compare the plurality of photoreceptor cells detected by the first detection unit and the plurality of photoreceptor cells detected by the second detection unit with each other; and
a display unit configured to display a symbol on each of the plurality of photoreceptor cells within one of the confocal image or the nonconfocal image displayed on a screen based on a comparison result obtained by the first comparison unit, wherein the symbol that is displayed on the photoreceptor cell detected from both the confocal image and the nonconfocal image, and the symbol that is displayed on the photoreceptor cell detected from the nonconfocal image but not detected from the confocal image differ in a color and/or a shape.

2. An ophthalmic apparatus according to claim 1, further comprising a second comparison unit configured to compare a first comparison result and a second comparison result with each other,
the first comparison result being a comparison result, which is obtained by the first comparison unit, between photoreceptor cells detected by the first detection unit from a first confocal image and photoreceptor cells detected by the second detection unit from a first nonconfocal image, the first confocal image and the first nonconfocal image being acquired by the acquisition unit at a first time,
the second comparison result being a comparison result, which is obtained by the first comparison unit, between photoreceptor cells detected by the first detection unit from a second confocal image and photoreceptor cells detected by the second detection unit from a second nonconfocal image, the second confocal image and the second nonconfocal image being acquired by the acquisition unit at a second time different from the first time
the display unit being configured to further display, based on a comparison result obtained by the second comparison unit, the symbol on the photoreceptor cell within one of the first confocal image or the first nonconfocal image displayed on the screen, the symbol including (A) a first symbol which indicates a photoreceptor cell that cannot be detected from the confocal image but can be detected from the nonconfocal image at the first time, but cannot be detected from the confocal image and the nonconfocal image at the second time, and (B) a second symbol which indicates a photoreceptor cell that can be detected from both the confocal image and the nonconfocal image at the first time, but cannot be detected from the confocal image or the nonconfocal image at the second time.

3. An ophthalmic apparatus according to claim 1, further comprising
an adapted optics scanning laser ophthalmoscope configured to capture the confocal image and the nonconfocal image,
wherein the acquisition unit acquire the confocal image and the nonconfocal image from the adapted optics scanning laser ophthalmoscope.

4. A control method for an ophthalmic apparatus, comprising:
an acquisition step of acquiring a confocal image and a nonconfocal image of an eye to be inspected based on a return light from the eye to be inspected, wherein the confocal image is generated from a beam of a central part of the return light and the nonconfocal image is generated from a beam of a surround part surrounding the central part of the return light;
a first detection step of detecting a plurality of photoreceptor cells of the eye to be inspected from the confocal image and a plurality of outer segments of photoreceptor cells;
a second detection step of detecting a plurality of photoreceptor cells of the eye to be inspected from the nonconfocal image and a plurality of inner segments and outer segments of photoreceptor cells;
a first comparison step of comparing the plurality of photoreceptor cells detected in the first detection step and the plurality of photoreceptor cells detected in the second detection step with each other; and
a display step of displaying a symbol on each of the plurality of photoreceptor cells within one of the confocal image or the nonconfocal image displayed on a screen based on a comparison result from the first comparison step, wherein the symbol that is displayed on the photoreceptor cell detected from both the confocal image and the nonconfocal image, and the symbol that is displayed on the photoreceptor cell detected from the nonconfocal image but not detected from the confocal image differ in a color and/or a shape.

5. A control method for an ophthalmic apparatus according to claim 4, further comprising a second comparison step of comparing a first comparison result and a second comparison result with each other,
the first comparison result being a comparison result, which is obtained in the first comparison step, between photoreceptor cells detected in the first detection step from a first confocal image and photoreceptor cells detected in the second detection step from a first nonconfocal image, the first confocal image and the first nonconfocal image being acquired in the acquisition step at a first time,
the second comparison result being a comparison result, which is obtained in the first comparison step, between photoreceptor cells detected in the first detection step from a second confocal image and photoreceptor cells detected in the second detection step from a second nonconfocal image, the second confocal image and the second nonconfocal image being acquired in the acquisition step at a second time different from the first time,
the display step comprising further displaying, based on a comparison result obtained in the second comparison step, the symbol on the photoreceptor cell within one of the first confocal image or the first nonconfocal image displayed on the screen, the symbol including (A) a first symbol which indicates a photoreceptor cell that cannot be detected from the confocal image but can be detected from the nonconfocal image at the first time, but cannot be detected from the confocal image and the nonconfocal image at the second time, and (B) a second symbol which indicates a photoreceptor cell that can be detected from both the confocal image and the nonconfocal image at the first time, but cannot be detected from the confocal image or the nonconfocal image at the second time.

6. A non-transitory tangible medium having recorded thereon a program for causing a computer to perform each of the steps of the control method for an ophthalmic apparatus of claim 5.

7. A storage medium storing a program for causing a computer to perform each of the steps of the control method for an ophthalmic apparatus of claim 4.

* * * * *